(12) United States Patent
Jenquin et al.

(10) Patent No.: US 7,861,756 B2
(45) Date of Patent: Jan. 4, 2011

(54) STAGGERED CUTTING KNIFE

(75) Inventors: Peter J. Jenquin, Plymouth, WI (US); John A. McCabe, Sheboygan Falls, WI (US); Thomas R. Coose, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 528 days.

(21) Appl. No.: 11/801,020

(22) Filed: May 8, 2007

(65) Prior Publication Data

US 2007/0284048 A1 Dec. 13, 2007

Related U.S. Application Data

(62) Division of application No. 10/828,095, filed on Apr. 20, 2004, now abandoned.

(51) Int. Cl.
*B32B 37/20* (2006.01)

(52) U.S. Cl. .................. 156/496; 156/494; 156/525; 156/526

(58) Field of Classification Search .............. 156/161, 156/163, 164, 179, 229, 265, 290, 291, 300, 156/301, 302, 494, 496, 525, 526
See application file for complete search history.

(56) References Cited

U.S. PATENT DOCUMENTS

| | | |
|---|---|---|
| 135,145 A | 1/1873 | Murphy |
| 293,253 A | 2/1884 | Purvis |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |

(Continued)

FOREIGN PATENT DOCUMENTS

BE 1007854 11/1995

(Continued)

OTHER PUBLICATIONS

U.S. Appl. No. 10/828,095; Office Communication, Restriction Requirement; Oct. 5, 2005; 5pgs.

(Continued)

*Primary Examiner*—George R Koch, III
(74) *Attorney, Agent, or Firm*—Ryan Krumholz & Manion, S.C.

(57) ABSTRACT

A method and apparatus for producing disposable undergarments having areas of defined elastic material is disclosed. The method provides for staggered cutting knives for severing the elastic material, which results in less necessary material used in the construction of the undergarments.

4 Claims, 5 Drawing Sheets

U.S. PATENT DOCUMENTS

| | | |
|---|---|---|
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,016,582 A | 6/1962 | Joa |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |

| Patent No. | Kind | Date | Inventor |
|---|---|---|---|
| 4,603,800 | A | 8/1986 | Focke et al. |
| 4,614,076 | A | 9/1986 | Rathemacher |
| 4,619,357 | A | 10/1986 | Radzins et al. |
| 4,634,482 | A | 1/1987 | Lammers |
| 4,641,381 | A | 2/1987 | Heran et al. |
| 4,642,150 | A | 2/1987 | Stemmler |
| 4,642,839 | A | 2/1987 | Urban |
| 4,650,530 | A | 3/1987 | Mahoney et al. |
| 4,663,220 | A | 5/1987 | Wisneski et al. |
| 4,672,705 | A | 6/1987 | Bors et al. |
| 4,675,062 | A | 6/1987 | Instance |
| 4,693,056 | A | 9/1987 | Raszewski |
| 4,701,239 | A | 10/1987 | Craig |
| 4,723,698 | A | 2/1988 | Schoonderbeek |
| 4,726,874 | A | 2/1988 | VanVliet |
| 4,726,876 | A | 2/1988 | Tomsovic, Jr. |
| 4,743,241 | A | 5/1988 | Igaue et al. |
| 4,751,997 | A | 6/1988 | Hirsch |
| 4,753,429 | A | 6/1988 | Irvine et al. |
| 4,756,141 | A | 7/1988 | Hirsch et al. |
| 4,764,325 | A | 8/1988 | Angstadt |
| 4,765,780 | A | 8/1988 | Angstadt |
| 4,776,920 | A | 10/1988 | Ryan |
| 4,777,513 | A | 10/1988 | Nelson |
| 4,782,647 | A | 11/1988 | Williams et al. |
| 4,785,986 | A | 11/1988 | Daane et al. |
| 4,795,510 | A | 1/1989 | Wittrock et al. |
| 4,798,353 | A | 1/1989 | Peugh |
| 4,801,345 | A | 1/1989 | Dussaud et al. |
| 4,802,570 | A | 2/1989 | Hirsch et al. |
| 4,840,609 | A | 6/1989 | Jones et al. |
| 4,845,964 | A | 7/1989 | Bors et al. |
| 4,864,802 | A | 9/1989 | D'Angelo |
| 4,880,102 | A | 11/1989 | Indrebo |
| 4,888,231 | A | 12/1989 | Angstadt |
| 4,892,536 | A | 1/1990 | DesMarais et al. |
| 4,904,440 | A | 2/1990 | Angstadt |
| 4,908,175 | A | 3/1990 | Angstadt |
| 4,909,019 | A | 3/1990 | Delacretaz et al. |
| 4,925,520 | A | 5/1990 | Beaudoin et al. |
| 4,927,322 | A | 5/1990 | Schweizer et al. |
| 4,927,582 | A | 5/1990 | Bryson |
| 4,937,887 | A | 7/1990 | Schreiner |
| 4,963,072 | A | 10/1990 | Miley et al. |
| 4,987,940 | A | 1/1991 | Straub et al. |
| 4,994,010 | A | 2/1991 | Doderer-Winkler |
| 5,000,806 | A | 3/1991 | Merkatoris et al. |
| 5,021,111 | A | 6/1991 | Swanson |
| 5,025,910 | A | 6/1991 | Lasure et al. |
| 5,045,039 | A | 9/1991 | Bay |
| 5,062,597 | A | 11/1991 | Martin et al. |
| 5,064,179 | A | 11/1991 | Martin |
| 5,064,492 | A | 11/1991 | Friesch |
| 5,080,741 | A | 1/1992 | Nomura et al. |
| 5,094,658 | A | 3/1992 | Smithe et al. |
| 5,096,532 | A | 3/1992 | Neuwirth et al. |
| 5,108,017 | A | 4/1992 | Adamski et al. |
| 5,109,767 | A | 5/1992 | Nyfeler et al. |
| 5,110,403 | A | 5/1992 | Ehlert |
| 5,127,981 | A | 7/1992 | Straub et al. |
| 5,131,525 | A | 7/1992 | Musschoot |
| 5,133,511 | A | 7/1992 | Mack et al. |
| 5,147,487 | A | 9/1992 | Nomura et al. |
| 5,163,594 | A | 11/1992 | Meyer |
| 5,171,239 | A | 12/1992 | Igaue et al. |
| 5,176,244 | A | 1/1993 | Radzins et al. |
| 5,183,252 | A | 2/1993 | Wolber et al. |
| 5,188,627 | A | 2/1993 | Igaue et al. |
| 5,190,234 | A | 3/1993 | Ezekiel |
| 5,195,684 | A | 3/1993 | Radzins |
| 5,203,043 | A | 4/1993 | Riedel |
| 5,213,645 | A | 5/1993 | Nomura et al. |
| 5,222,422 | A | 6/1993 | Benner, Jr. et al. |
| 5,223,069 | A | 6/1993 | Tokuno et al. |
| 5,226,992 | A | 7/1993 | Morman |
| 5,246,433 | A | 9/1993 | Hasse et al. |
| 5,252,170 | A | 10/1993 | Schaupp |
| 5,267,933 | A | 12/1993 | Precoma |
| 5,273,228 | A | 12/1993 | Yoshida et al. |
| 5,308,345 | A | 5/1994 | Herrin |
| 5,328,438 | A | 7/1994 | Crowley |
| 5,340,424 | A | 8/1994 | Matsushita |
| 5,368,893 | A | 11/1994 | Sommer et al. |
| 5,407,513 | A | 4/1995 | Hayden et al. |
| 5,415,649 | A | 5/1995 | Watanabe et al. |
| 5,421,924 | A | 6/1995 | Ziegelhoffer et al. |
| 5,424,025 | A | 6/1995 | Hanschen et al. |
| 5,429,576 | A | 7/1995 | Doderer-Winkler |
| 5,435,802 | A | 7/1995 | Kober |
| 5,449,353 | A | 9/1995 | Watanabe et al. |
| 5,464,401 | A | 11/1995 | Hasse et al. |
| 5,486,253 | A | 1/1996 | Otruba |
| 5,494,622 | A | 2/1996 | Heath et al. |
| 5,531,850 | A | 7/1996 | Herrmann |
| 5,540,647 | A | 7/1996 | Weiermann et al. |
| 5,545,275 | A | 8/1996 | Herrin et al. |
| 5,545,285 | A | 8/1996 | Johnson |
| 5,552,013 | A | 9/1996 | Ehlert et al. |
| 5,556,360 | A | 9/1996 | Kober et al. |
| 5,556,504 | A | 9/1996 | Rajala et al. |
| 5,560,793 | A | 10/1996 | Ruscher et al. |
| 5,602,747 | A | 2/1997 | Rajala |
| 5,624,420 | A | 4/1997 | Bridges et al. |
| 5,624,428 | A | 4/1997 | Sauer |
| 5,628,738 | A | 5/1997 | Suekane |
| 5,634,917 | A | 6/1997 | Fujioka et al. |
| 5,643,165 | A | 7/1997 | Klekamp |
| 5,643,396 | A | 7/1997 | Rajala et al. |
| 5,645,543 | A | 7/1997 | Nomura et al. |
| 5,659,229 | A | 8/1997 | Rajala |
| 5,660,657 | A | 8/1997 | Rajala et al. |
| 5,660,665 | A | 8/1997 | Jalonen |
| 5,683,376 | A | 11/1997 | Kato et al. |
| RE35,687 | E | 12/1997 | Igaue et al. |
| 5,693,165 | A | 12/1997 | Schmitz |
| 5,699,653 | A | 12/1997 | Hartman et al. |
| 5,707,470 | A | 1/1998 | Rajala et al. |
| 5,711,832 | A | 1/1998 | Glaug et al. |
| 5,725,518 | A | 3/1998 | Coates |
| 5,745,922 | A | 5/1998 | Rajala et al. |
| 5,746,869 | A | 5/1998 | Hayden et al. |
| 5,749,989 | A | 5/1998 | Linman et al. |
| 5,788,797 | A | 8/1998 | Herrin et al. |
| 5,817,199 | A | 10/1998 | Brennecke et al. |
| 5,829,164 | A | 11/1998 | Kotitschke |
| 5,836,931 | A | 11/1998 | Toyoda et al. |
| 5,858,012 | A | 1/1999 | Yamaki et al. |
| 5,865,393 | A | 2/1999 | Kreft et al. |
| 5,868,727 | A | 2/1999 | Barr et al. |
| 5,876,027 | A | 3/1999 | Fukui et al. |
| 5,876,792 | A | 3/1999 | Caldwell |
| 5,879,500 | A | 3/1999 | Herrin et al. |
| 5,902,431 | A | 5/1999 | Wilkinson et al. |
| 5,932,039 | A | 8/1999 | Popp et al. |
| 5,938,193 | A | 8/1999 | Bluemle et al. |
| 5,964,390 | A | 10/1999 | Borresen et al. |
| 5,964,970 | A | 10/1999 | Woolwine et al. |
| 6,036,805 | A | 3/2000 | McNichols |
| 6,043,836 | A | 3/2000 | Kerr et al. |
| 6,050,517 | A | 4/2000 | Dobrescu et al. |
| 6,074,110 | A | 6/2000 | Verlinden et al. |
| 6,076,442 | A | 6/2000 | Arterburn et al. |
| 6,098,249 | A | 8/2000 | Toney et al. |
| 6,123,792 | A | 9/2000 | Samida et al. |
| 6,171,432 | B1 | 1/2001 | Brisebois et al. |
| 6,183,576 | B1 | 2/2001 | Couillard et al. |

| | | |
|---|---|---|
| 6,210,386 B1 | 4/2001 | Inoue |
| 6,212,859 B1 | 4/2001 | Bielik, Jr. et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,587 B1 | 8/2001 | Borresen et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,523,595 B1 | 2/2003 | Milner et al. |
| 6,524,423 B1 | 2/2003 | Hilt et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 * | 11/2003 | Parrish et al. ............... 156/265 |
| 6,656,309 B1 | 12/2003 | Parker et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,722,494 B2 | 4/2004 | Nakakado |
| 6,743,324 B2 | 6/2004 | Hargett et al. |
| 6,758,109 B2 | 7/2004 | Nakakado |
| 6,766,817 B2 | 7/2004 | da Silva |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,066,586 B2 | 6/2006 | da Silva |
| 7,077,393 B2 | 7/2006 | Ishida |
| 7,172,666 B2 | 2/2007 | Groves et al. |
| 7,195,684 B2 | 3/2007 | Satoh |
| 7,201,345 B2 | 4/2007 | Werner et al. |
| 7,214,174 B2 | 5/2007 | Allen et al. |
| 7,247,219 B2 | 7/2007 | O'Dowd |
| 7,587,966 B2 | 9/2009 | Nakakado et al. |
| 2001/0012813 A1 | 8/2001 | Bluemle |
| 2001/0017181 A1 | 8/2001 | Otruba et al. |
| 2002/0046802 A1 * | 4/2002 | Tachibana et al. ............ 156/209 |
| 2002/0059013 A1 | 5/2002 | Rajala et al. |
| 2002/0096241 A1 | 7/2002 | Instance |
| 2002/0125105 A1 | 9/2002 | Nakakado |
| 2003/0000620 A1 | 1/2003 | Herrin et al. |
| 2003/0015209 A1 | 1/2003 | Gingras et al. |
| 2003/0051802 A1 | 3/2003 | Hargett |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0121614 A1 | 7/2003 | Tabor |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0112517 A1 | 6/2004 | Groves et al. |
| 2004/0164482 A1 | 8/2004 | Edinger |
| 2005/0000628 A1 | 1/2005 | Norrby |
| 2005/0022476 A1 | 2/2005 | Hamer et al. |
| 2005/0077418 A1 | 4/2005 | Werner et al. |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0 048 011 | 3/1982 |
| EP | 0089106 | 9/1983 |
| EP | 0099732 | 2/1984 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0 901 780 | 3/1999 |
| EP | 0901780 | 3/1999 |
| EP | 990588 | 4/2000 |
| EP | 1132325 | 9/2001 |
| EP | 1199057 | 4/2002 |
| EP | 1272347 | 1/2003 |
| EP | 1571249 | 9/2005 |
| EP | 1619008 | 1/2006 |
| EP | 1707168 | 4/2006 |
| EP | 1726414 | 11/2006 |
| EP | 1941853 | 7/2008 |
| ES | 509706 | 11/1982 |
| ES | 520559 | 12/1983 |
| ES | 296211 | 12/1987 |
| FR | 2177355 | 11/1973 |

| | | |
|---|---|---|
| FR | 2255961 | 7/1975 |
| FR | 0206208 | 12/1986 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| JP | 4-28364 | 1/1992 |
| JP | 5-42180 | 2/1993 |
| JP | 5-76566 | 3/1993 |
| JP | 6-197925 | 7/1994 |
| JP | 6-26160 | 11/1994 |
| JP | 6-26161 | 11/1994 |
| JP | 10035621 | 2/1998 |
| JP | 10-277091 | 10/1998 |
| SE | 0602047 | 5/2007 |
| WO | WO9403301 | 2/1994 |
| WO | WO9747265 | 12/1997 |
| WO | WO 9747810 | 12/1997 |
| WO | WO9821134 | 5/1998 |
| WO | WO9907319 | 2/1999 |
| WO | WO 99/13813 | 3/1999 |
| WO | WO9932385 | 7/1999 |
| WO | WO9965437 | 12/1999 |
| WO | WO0143682 | 6/2001 |
| WO | WO0172237 | 10/2001 |
| WO | WO2004007329 | 1/2004 |
| WO | WO2005075163 | 1/2005 |

OTHER PUBLICATIONS

U.S. Appl. No. 10/828,095; Confirmation of Election; Amendment A; Oct. 19, 2005; 1pg.

U.S. Appl. No. 10/828,095; Office Communication, Restriction Requirement; Dec. 30, 2005.

U.S. Appl. No. 10/828,095; Response to Restriction Requirement; Amendment B; Feb. 27, 2006; 3pgs.

U.S. Appl. No. 10/828,095; Office Communication, May 18, 2006; 5pgs.

U.S. Appl. No. 10/828,095; Response to Office Action; Amendment C; Nov. 20, 2006; 5pgs.

U.S. Appl. No. 10/828,095; Petition For Withdrawal From Issue-Issue Fee Paid, Apr. 9, 2007; 1 pg.

U.S. Appl. No. 10/828,095; Request for Continued Examination, Apr. 9, 2007; 1pg.

U.S. Appl. No. 10/828,095; Office Communication, Aug. 8, 2007; 5pgs.

U.S. Appl. No. 10/828,095; Response to Office Action; Amendment D; Nov. 8, 2007; 5pgs.

U.S. Appl. No. 10/828,095; Final Office Communication, Jan. 25, 2008; 5pgs.

U.S. Appl. No. 10/828,095; Office Communication-Notice of Abandonment, Aug. 20, 2008; 2pgs.

U.S. Appl. No. 11/324,923; Notice of Allowance, Jan. 4, 2010; 5pgs.

U.S. Appl. No. 11/324,923; Non-Final Office Action, Apr. 2, 2009; 7pgs.

U.S. Appl. No. 11/324,923; Response to Office Action-Amendment A; Aug. 13, 2009; 7pgs.

U.S. Appl. No. 11/324,923; Notice of Non-Compliant Amendment; Oct. 6, 2009; 3pgs.

U.S. Appl. No. 11/324,923; Response to Notice of Non-Compliant Amendment; Oct. 14, 2009; 6pgs.

U.S. Appl. No. 11/324,923; Office Communication, Applicant: John A. McCabe; Apr. 2, 2009; pp. 9.

U.S. Appl. No. 11/324,923; Notice of Non-Compliant Amendment, Applicant: John A. McCabe; Oct. 6, 2009; pp. 3.

* cited by examiner

STAGGERED CUTTING KNIFE

RELATED APPLICATION

This application is a division of U.S. Ser. No. 10/828,095 filed Apr. 20, 2004, now abandonded.

BACKGROUND OF THE INVENTION

The present invention relates to disposable undergarments and more specifically, to methods and apparatuses for cutting and forming disposable undergarments.

Most disposable undergarments or diapers are currently formed having some areas of elasticity. The waist area, leg holes, and sides of a disposable garment preferably have some elastic qualities. The areas of elasticity, known as "fit gather" areas, provide for a snug fit on the wearer, such as a child.

It is advantageous for certain areas of the undergarment to be free of elastic material. For instance, it is not desirous to have the front and rear sections of the diaper contain elastic material. Such elastic material may be uncomfortable for the wearer, as it may cause the undergarment to unnecessarily bunch and be constricting to the wearer. Furthermore, undergarments, especially children's diapers, are also more commonly being designed with pictures or patterns on the front and/or rear of the diaper. Forming diapers without elastic material in these areas, or removal of the elastic material from these areas, prevents the pictures or patterns from being distorted, as the fit gather has the tendency to bunch up if elastic is present in those areas.

However, when the elastic material is removed from the diaper, it may cause unwanted elongation or stretching of the diaper, as the remaining elastic material may cause the other layers of material to be pulled apart at the area where the elastic material was removed. Such pulling and tension forces may weaken the diaper and may even cause the diaper to rip or tear.

Umebayashi, U.S. Pat. No. 6,554,815, addressed the above problem by cutting the elastic in the desired areas and placing a reinforcement sheet in those areas. The reinforcement sheet preferably has a design located on the sheet. However, if a design is not wanted, an extra piece of material is required to complete the process. Consequently the costs and materials of the diaper are unnecessarily increased.

SUMMARY OF THE INVENTION

The present invention alleviates the above problems by disclosing a new method for severing the elastic materials in the front or rear of the diaper. The present invention removes the necessity of using a reinforcement sheet of material that is present in prior garment designs. A staggered knife assembly is used to cut the elastic material. The staggered knife allows for the elastic material to be removed without requiring a reinforcing sheet and results in a more efficient and cost effective production process.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Figure 1:
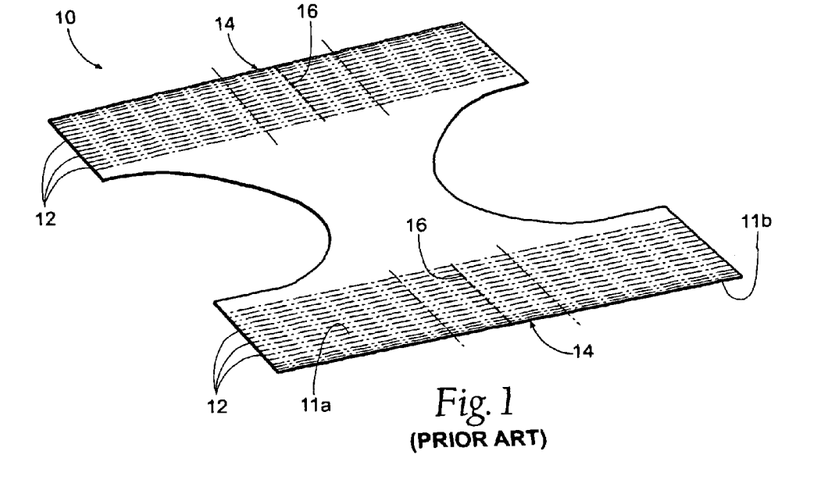
FIG. 1 is a perspective planar view disclosing a disposable undergarment blank made in accordance with the prior art.
Figure 2:
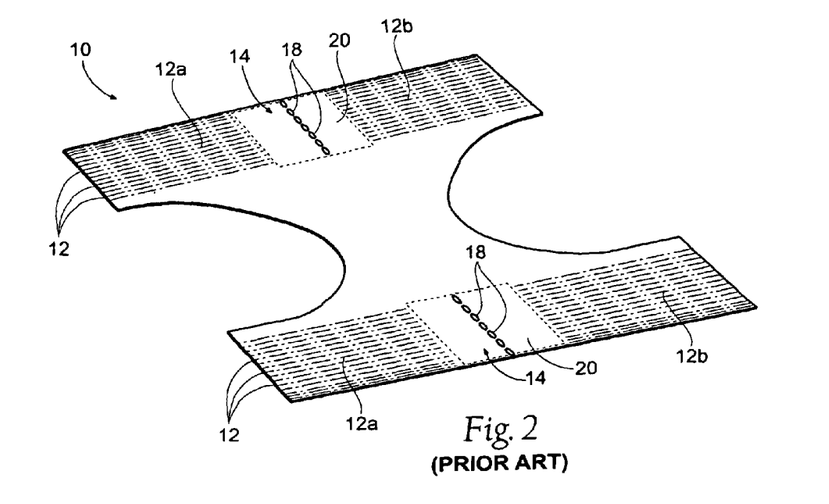
FIG. 2 is a perspective planar view of made in accordance with the prior art of FIG. 1, and having areas of elastic material removed.

FIGS. 1 and 2 show planar views of a disposable undergarment blank 10 made according to prior art techniques. The undergarment blank 10 has a plurality of laterally spaced elastic strands 12 extending widthwise of the undergarment blank 10. The elastic strands 12 are preferably intermittently glued between two layers 11a and 11b of nonwoven material. For design and comfort purposes, it is desired to remove the elastic strands 12 from a central area 14. As shown in FIG. 1, the prior art method for removing the strands 12 from the central area is to sever the strands 12 with a knife (not shown) along a single path, designated in FIG. 1 by the reference numeral 16.

Still referring to FIGS. 1 and 2, one of the layers of nonwoven material and the elastic strands 12 are severed along the knife path 16. After severing, the strands will snap away from the knife path 16, leaving the central area 14 devoid of elastic material 12. As shown in FIG. 2, once the elastic strands 12 are removed from the central area 14, a plurality of holes 18 will evolve along the knife path 16. The holes 18 are the product of the nonwoven material being subjected to outward forces supplied by remaining areas 12a and 12b of strands 12 existing at opposite sides of the knife path 16. If left unattended, the tension pulling outwardly from the holes 18 can cause the holes 18 to stretch and elongate, and possibly deform or tear apart the blank 10. To compensate for this force, the prior art provides a reinforcement sheet of material 20 that would be glued or fastened over the holes 18 (shown in phantom).

Figure 3:
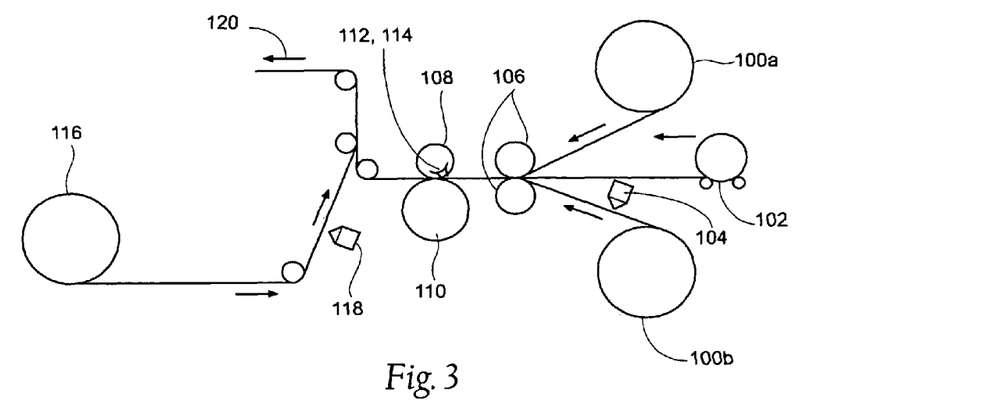
FIG. 3 is a schematic view of a method and apparatus that may be used to produce undergarments in accordance with the present invention.

A schematic view of a desired assembly process according to the present invention is shown in FIG. 3. A pair of nonwoven layers of material 100a and 100b and an elastic material 102 are provided. The layers 100a, 100b and 102 are used to form a fit gather laminate area for the eventual undergarment. An adhesive applicator 104 is shown, which will apply an adhesive material, such as a hot melt adhesive, onto one of the nonwoven layers of material 100a or 100b. The adhesive applicator 104 is arranged to provide adhesive material to at least a first portion of the nonwoven layers 100a or 100b, as necessary. The adhesive applicator 104 may be arranged in any way that will provide intermittent glue to the nonwoven layers 100a and 100b. The adhered first portions of 100a and 100b will also define a non-adhering second portion 100c, preferably in the central area of what will eventually become an individual garment blank 50 (see FIGS. 8 and 9). The nonwoven layers 100 and the elastic material 102 proceed towards a pair of pressing rolls 106, which press the three layers together and secures the three layers together in the first portion 100a, 100b of the nonwoven layers 100. After passing the pressing rolls 106, the layers 100 and 102 will pass through a severing station 80, described in FIGS. 6 and 11, and comprising a cutting roll 108 and an anvil roller 110, where the cutting roll will sever the elastic material in the second non-adhered portion 100c of the nonwoven layers 100. The anvil roller 110 provides resistance for the cutting roll 108 to act thereagainst.

Referring to FIG. 3, the cutting roll 108 has two blade assemblies 112 and 114 arranged to sever the layer 100a and the layer 102 of elastic material. The blade assemblies 112 and 114, which are staggered and designed preferably to not cut the same strands of elastic material 102 as one another, will be discussed in more detail in FIGS. 6-11. Further along the assembly in FIG. 3, a backing layer 116 is introduced, represented on the left-hand side of the schematic view. The backing layer 116 passes an adhesive applicator 118, similar to the adhesive applicator 104. The backing layer 116 than proceeds towards the layer consisting of the nonwoven layers 100a and 100b and the elastic material 102, whereby all the layers are combined as a resultant layer 120. The resultant layer 120 is comparable to a layer formed by the prior art, without needing to add a reinforcing sheet of material. Furthermore, since, in the present invention, there is no need to adhere reinforcing material to the nonwoven layers, there is less of a chance that the undergarment will be improperly formed. If one wishes to add designs to the process, they may be added before or after the resultant layer 120, which also allows for an added degree of freedom for design purposes over the prior art.

Figure 4:
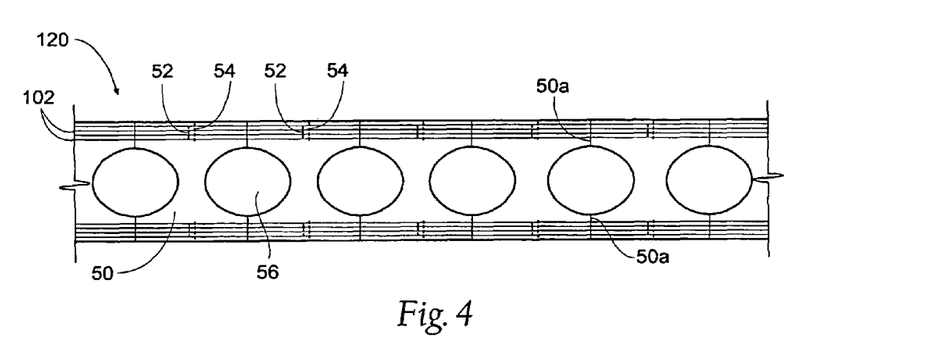
FIG. 4 is a planar perspective view of a web of adjacent undergarment blanks and illustratively severing cuts performed at selected areas of adhering elastic strands, forming a layer therein, and further of through severing cuts separating the web into a plurality of adjacent undergarment blanks.

FIG. 4 shows a planar view of the resultant layer 120, which comprise the nonwoven layers 100a, 100b, and the layer of elastic material 102 placed intermediate of the nonwoven layers 100a and 100b. As shown, the layer of elastic material 102 comprises a plurality of stretchable elastic elements. For simplicity, the layer of elastic material and the elastic elements will both be referred to with reference numeral 102. Knife paths 52 and 54 show where the blade assemblies 112 and 114 severed the elastic elements. The resultant layer 120 is shown as a plurality of the blanks 50, with the edges of the blanks 50 defined by lines 50a. Leg holes 56 are cut from the layer 120, preferably after the resultant layer 120 has been formed as previously described.

Figure 5:
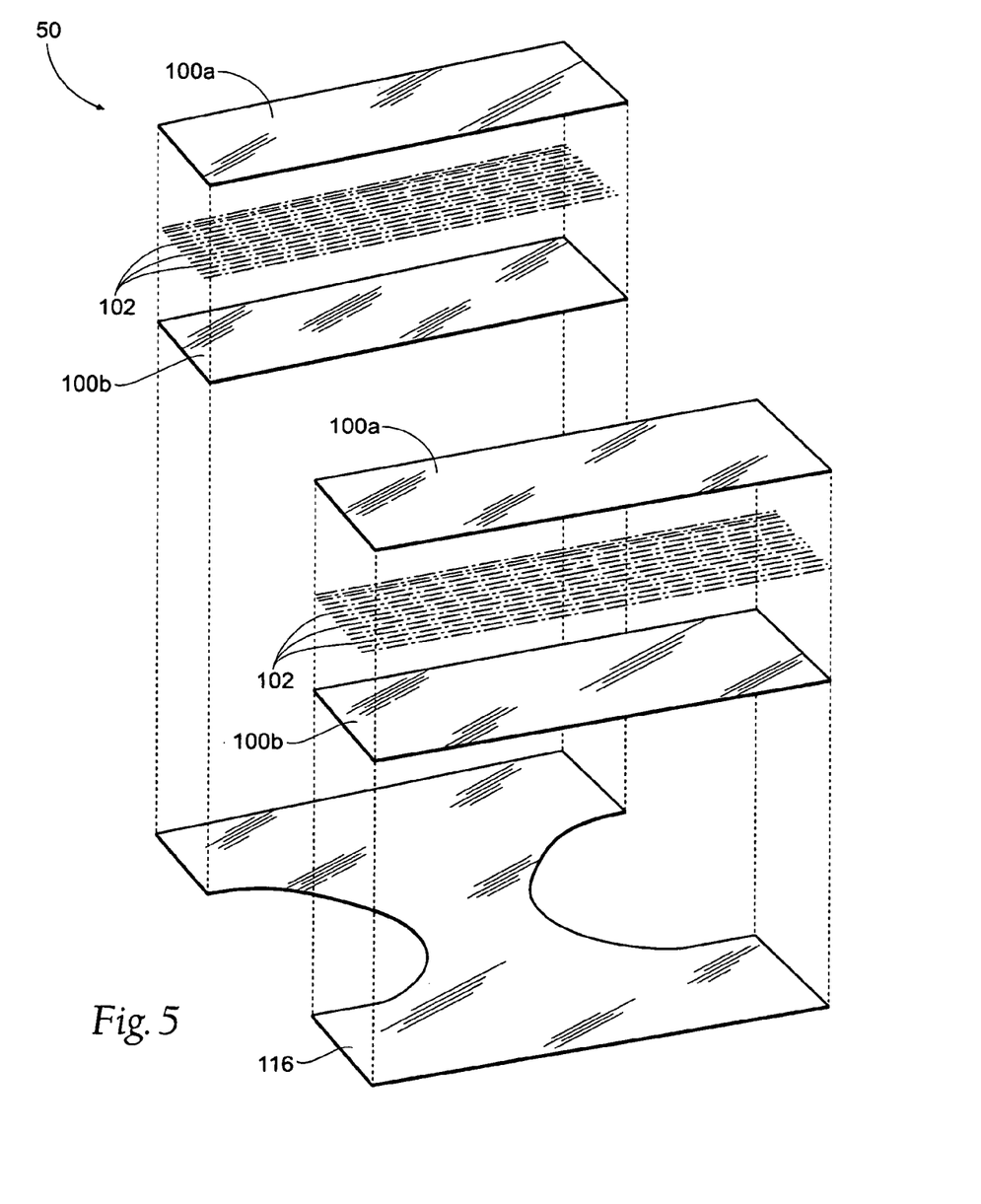
FIG. 5 is an exploded view of a typical undergarment blank produced in accordance with the present invention.

Referring to FIG. 5, an exploded view of the undergarment blank 50 utilizing the present invention is shown. The knife paths 52 and 54 represent the blade assemblies 112 and 114, shown in FIG. 3. The knife paths 52 and 54 are staggered, showing that the blade assemblies 112 and 114 sever separate strands of elastic material 102. The elastic material 102, as shown, may be layered on a substrate material to provide sufficient structure and alignment for the elastic strands 102. The knife paths 52 and 54 are spaced far enough apart from each other that elongation of the individual cuts, as seen in the prior art (FIG. 2) is minimized, and the strength of the nonwoven layers remains such that a reinforcement panel or sheet is not necessary. Although it is possible for the knife paths 52 and 54 to overlap one another, it is not preferable to have complete overlap of the paths, as such an arrangement would lead to the problems caused by the prior art (see FIG. 2). The knife paths 52 and 54 are shown severing the central elastic layer 102 and the nonwoven layer 100a.

Nonwoven layer 100a can be cut through, but is not required to be cut through. The knife blades are able to pinch the elastic through the nonwoven layer 100a without actually severing the nonwoven layer 100a. The pinching action is enough to cause the elastic to break apart without actually cutting through the nonwoven layer 100a.

Although it is possible also to sever the nonwoven layer 100b, it is not necessary for the present invention. Likewise, it should be understood that layer 100a is the layer nearest the to the blade assemblies 112 and 114 (see FIG. 3) and should not be limited to any specific spatial orientation.

Figure 6:
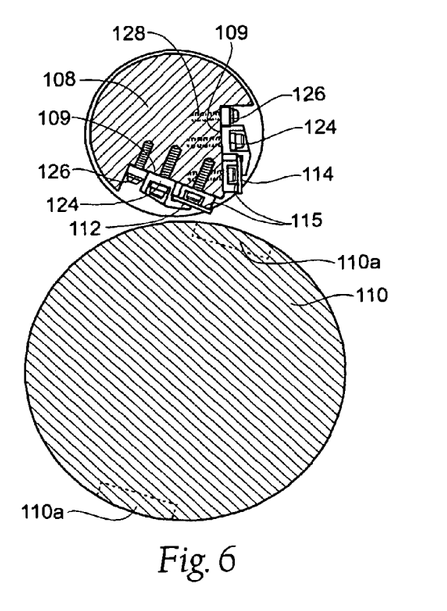
FIG. 6 is a cross-sectional view of an elastic strand severing station forming a section of the apparatus fabricated in accordance with the present invention.

FIG. 6 is a close-up view of the cutting or knife roll 108 and the anvil roller 110. As shown, the blade assemblies 112 and 114 are distinct and separate blades. The blade assemblies 112 and 114 are each provided with an elongated base 115 (see also FIG. 10) extending in an axial elevation across at least a machined insert portion 108p (see FIGS. 10 and 11) of the cutting or severing roll 108. The assemblies 112 and 114 are preferably of flat steel stock arranged to lie flat against a machined flat surface 109 of the insert area 108p. The anvil roller 110 may contain carbide inserts 110a. If so, the assemblies 112 and 114 should be arranged so that they only make contact with the carbide inserts 110a and not the rest of the anvil roller. The blade assemblies 112 and 114 are held in place by respective clamp bars 124. To further insure the blade assemblies 112 and 114 are securely held in place, a respective backup wedge 126 is located behind each of the respective clamp bars 124. Preferably bolts 128 are used to secure the noted elements to the knife roll 108, but any securing means that will not interfere with the cutting process may be used.

Figure 8:
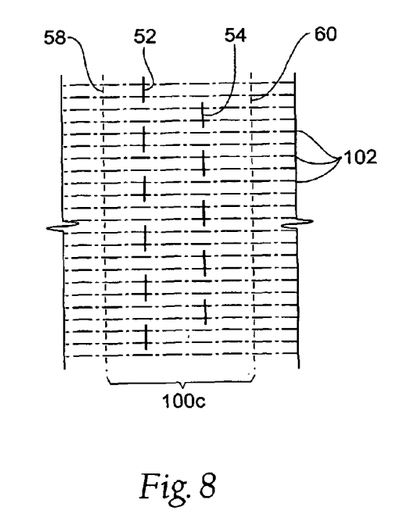
FIGS. 8 and 9 are enlarged sectional views of selected areas the blank of FIG. 5 with a section of elastic removed.
Figure 9:
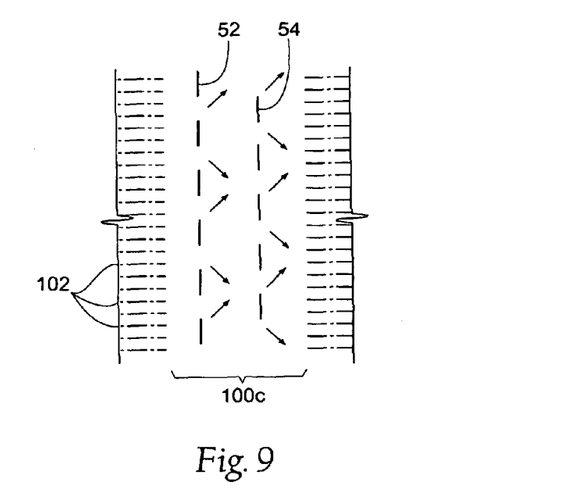

Still referring to FIG. 6, the blade assemblies 112 and 114 are circumferentially spaced apart for a preselected distance sufficient to sever the layers 100a and 102 along knife paths 52 and 54 for removal of elastic material located in the non-adhered portion 100c (see FIGS. 8 and 9). The blade assemblies 112 and 114 are at spaced apart locations on the cutting roll 108, which results in the staggered pattern of FIG. 4. As previously stated, the blade assemblies 112 and 114 are spaced far enough apart from each other to thereby minimize the tension and elongation effects of the cuts 52 and 54 that are made in the undergarment blank 50 (see FIGS. 8 and 9). The blade assemblies 112 and 114 may also be positioned to comply with one or more knife assemblies. For example another set of blades may be employed to cut more than one area of elastic concurrently. Such an arrangement may be advantageous if, as the knife paths 52 and 54 of FIG. 4 indicate, elastic material is desired to be removed from both the top and bottom half of the blank 50. The blade assemblies 112 and 114 are shown angled towards one another. While no specific angle is needed between the blade assemblies 112 and 114, it is preferable that the blade assemblies 112 and 114 are arranged on the cutting roll 108 relatively near each other so that they will easily cut the layers 100a and 102 while the cutting roll 108 is rotating, and, also, so that the blade assemblies 112 and 114. Further, this will assist in keeping the cuts made by the blade assemblies 112 and 114 within the non-adhered portion 102c of the elastic elements 102 (see FIGS. 5, 8, and 9).

Figure 7:
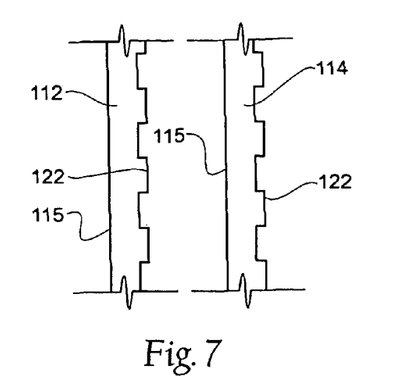
FIG. 7 is a diagrammatic view used herein to illustrate the preferred relative location of adjacent severing knife blades of the apparatus station shown in FIG. 6.

FIG. 7 is a further schematic view of the blade assemblies 112 and 114 in FIG. 6. A plurality of teeth or individual knife blades 122 is located on each of the blade assemblies 112 and 114. The teeth 122 are preferably in a saw tooth pattern as shown, connected to the knife assemblies 112 and 114 by the respective supporting bases 115. It should also be understood that the teeth 122 might consist of a plurality of individual knife blades that lie in a common plane, as opposed to a single blade. Thus, the teeth 122 potentially could comprise separate blades fastened to the cutting roll 108. The teeth 122 are preferably aligned so that the teeth of blade 112 do not overlap the teeth of blade 114 when severing the elastic strands 102, as was discussed with respect to FIG. 5 (see also FIGS. 8 and 9). However, if elastics are very close to each other, the teeth 122 may overlap slightly to prevent elastics from swimming between cutting planes.

The teeth 122 are further designed to insure that all of the elastic strands 102 are severed by one or the other of the two blades. The blade assemblies 112 and 114 will not normally be directionally spaced apart as shown in FIG. 7 (see FIGS. 6 and 10). However, FIG. 7 is used to exemplify the staggered relationship of the blade assemblies 112 and 114.

FIG. 8 is a close-up view of the blank 50 and the knife paths 52 and 54. The knife paths 52 and 54 provide for removal of the elastic strands 102 in the non-adhered portion 100c, preferably located centrally of the blank 50. The non-adhered portion 100c is defined by opposing sides 58 and 60, which represent the extent to which the adhesive applicator 104 applied an adhesive to the blank 50, as described with respect to FIG. 3. The opposing sides 58 and 60 do not need to be straight or parallel to one another.

FIG. 9 shows the benefit of the cuts 52 and 54. The non-adhered portion 100c is now shown devoid of any elastic strands 102. As indicated by the arrows, the tension resulting from the cuts is not focused in one particular direction or area, but is spread out, thereby resulting in less force to pull apart the material. The potential of holes being formed along the cut lines is minimized. If the tension and pulling forces are not minimized according to the present invention, the nonwoven material may pull apart, as was evident in the prior art of FIG. 2. As was previously describe with respect to the schematic of FIG. 3, a backing layer 116 may be applied to the blank 50 without needing to place an intermediate reinforcing layer onto the blank 50.

Figure 10:
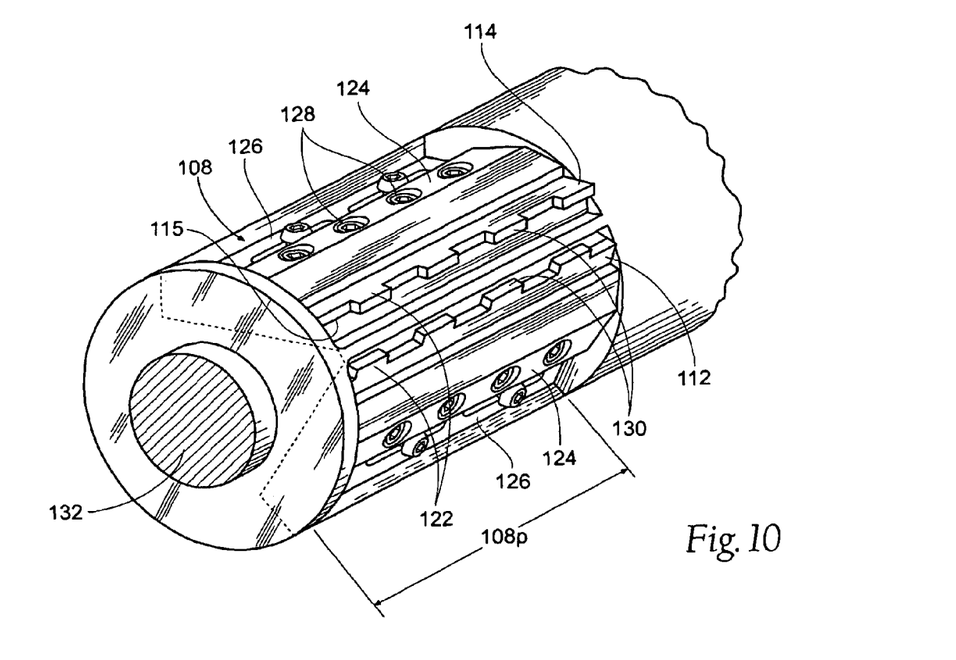
FIG. 10 is a perspective view of a severing roller knife used in connection with a severing station fabricated according with the teachings of the present invention.

A perspective view of the knife roll 108 is presented in FIG. 10. The individual knife blades 122 have a sharpened edge 130 that intersects and cuts one of the nonwoven layers 100 and the elastic material 102. While the knife roll could be arranged to cut through both of the nonwoven layers 100a and 100b, it is not necessary. The clamp bars 124 and the backup wedges 126 can be seen more clearly holding the blade assemblies 112 and 114 in place. The supporting bases 115 of the assemblies 112 and 114 are secured to the knife roll, preferably with the bolts 128. A central axis 132 allows the knife roll 108 to rotate during the production process.

Figure 11:
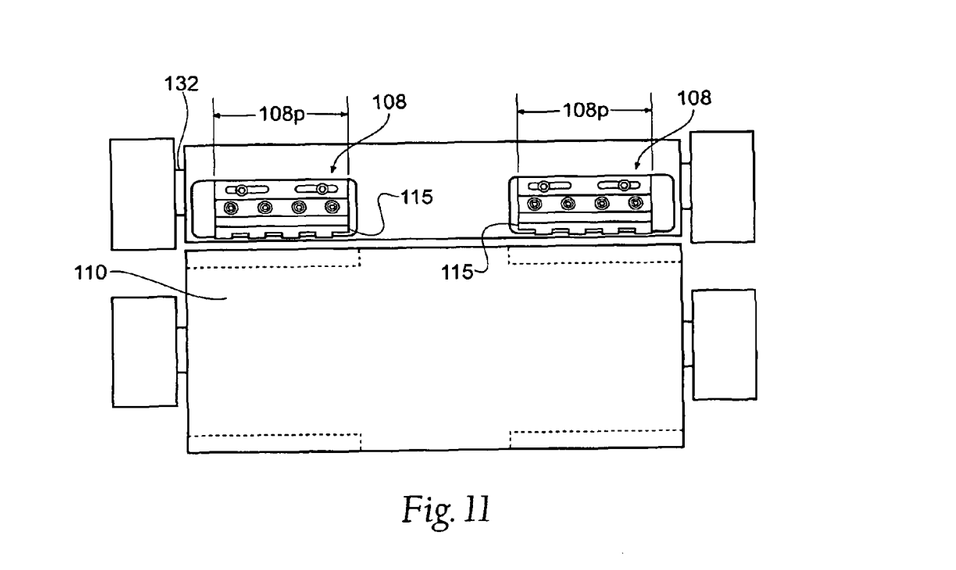
FIG. 11 is a front view of a roller and anvil roller of a severing station used according to the teachings of the present invention.

FIG. 11 shows a front view of a severing station 70 utilizing the knife roll 108 and the anvil 110. In this embodiment, the cutting station consists of two cutting rolls 108 that interact with the anvil 110. The severing station may apply more anvils 110 and more or fewer knife rolls 108, as necessary. The arrangement may allow for two assembly lines to rub simultaneously. As previously noted, the supporting bases 115 extend axially across the portion 108p of the cutting roll 108. The central axis 132 rotates the knife rolls 108 and the assemblies 112 and 114. The cutting roll 108 and the anvil roller 110 preferably are spaced apart so that the nonwoven layer 100a and the layer of elastic material 102 are severed when passing the cutting station, but the nonwoven layer 100b is not cut.

FIG. 11 provides a possible arrangement for the severing station 70. However, different designs would fall within the scope of the present invention. For instance, the cutting roll 108 could potentially be a flat stamp or plate that would press the blade assemblies 112 and 114 into the elastic material 102. Similarly, the assemblies 112 and 114 could be located on separate pistons or drive shafts that would also provide the cutting arrangement described of the assemblies 112 and 114. Provided that the severing station 70 or the cutting roll 108 can provide the described staggered arrangement, the station 70 or roll 108 should be understood as within the scope of the present invention. Likewise, the anvil 110 should be understood to encompass a structure that will provide resistance for the assemblies 112 and 114 to act against.

The process is advantageous not only because it requires less raw materials than prior processes, which provides for a more efficient and cost effective process, but also allows for a more adaptive process. For instance, disposable undergarments are made for children and, also, adults. Designs and patterns on the undergarments, while fashionable on children's undergarments, are not necessarily desirous on adult undergarments. Consequently, assembly lines that may be used for both adult and child undergarments would have to remove the designs that were applied to the children's diapers. Previous arrangements placed such designs on the reinforcement sheet of material. A different reinforcement sheet of material without a design would have to be introduced into the assembly process, causing extra downtime. However, since the present invention does not require a reinforcement sheet in the assembly process, any designs may be easily added or removed from the process with less downtime than previously used.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A knife assembly for an apparatus used in the manufacture of a garment having a fit gather laminate area extending widthwise of said garment, said area comprising a plurality of layers, said layers including a layer of non-woven material and an adjacent layer of a plurality of longitudinally widthwise stretchable elastic elements laterally spaced lengthwise relative to said garment, said knife assembly comprising:

a plurality of knife blades having cutting edges extending lengthwise across said fit gather laminate area, said plurality of blades including:

a first pair of spaced apart knife blades located in a common plane removably carried by a rotating body; and a second pair of spaced apart knife blades located in a second common plane removably carried by said rotating body and being in an alternatively staggered relationship to a respective knife blade lying in said first common plane;

a knife free-zone positioned between said first and said second pair of spaced apart knife blades in a cross machine direction; and support means securing said knife blades in said staggered relationship; and said first pair of spaced apart knife blades acting upon a first line of intended elastic severing in a machine direction;

said second pair of spaced apart knife blades acting upon a second line of intended elastic severing in the machine direction;

said first and second lines of intended elastic severing not overlapping in the cross-machine direction.

2. The knife assembly according to claim 1 wherein said support means comprises a roll bar.

3. A severing station in a continuous garment production assembly for severing elastic material in said garment having a fit gather laminate area, the station comprising:
- a cutting roll;
- a plurality of knife blades located on said cutting roll, said knife blades having cutting edges extending lengthwise across said fit gather laminate area, said plurality of blades including:
- a first pair of spaced apart knife blades located in a common plane; and
- a second pair of spaced apart knife blades located in a second common plane and being in an alternatively staggered relationship to a respective knife blade lying in said first common plane; and
- an anvil roller;
- said first pair of knife blades spaced apart to define a first segment of intended severing, a first zone of no intended severing between said spaced apart relationship of said first pair of knife blades; and a second segment of intended severing;
- said second pair of knife blades spaced apart to define a third segment of intended severing, a second zone of no intended severing between said spaced apart relationship of said second pair of knife blades; and a second zone of intended severing;
- a knife free-zone positioned between said first and said second pair of spaced apart knife blades in a cross machine direction.

4. The severing station according to claim 3, wherein said anvil roller further comprises at least one carbide insert, said carbide insert providing an area for said knife blades to act against.

* * * * *